United States Patent [19]

Wood

[11] Patent Number: 4,606,624
[45] Date of Patent: Aug. 19, 1986

[54] REFRACTOR HAVING SIMPLIFIED CYLINDER LENS ASSEMBLY

[75] Inventor: David E. Wood, Grove City, Ohio

[73] Assignee: R. H. Burton Company, Grove City, Ohio

[21] Appl. No.: 541,552

[22] Filed: Oct. 13, 1983

[51] Int. Cl.$^4$ ............................................. A61B 3/02
[52] U.S. Cl. ..................................... 351/234; 351/235
[58] Field of Search ................................. 351/234, 235

[56] References Cited

U.S. PATENT DOCUMENTS

| | | |
|---|---|---|
| 2,322,878 | 6/1943 | Peck et al. .......................... 351/235 |
| 2,923,200 | 2/1960 | Wright . |
| 2,938,426 | 5/1960 | Armbruster et al. . |
| 2,968,213 | 1/1961 | Wright et al. . |
| 2,995,065 | 8/1961 | Wright et al. . |
| 3,498,699 | 3/1970 | Wilkinson . |

Primary Examiner—Rodney B. Bovernick
Assistant Examiner—P. M. Dzierzynski
Attorney, Agent, or Firm—Mueller and Smith

[57] ABSTRACT

Disclosed is a refractor of the type having a housing which has patient eye position for viewing along a sight axis extendible therethrough, a pair of superimposed cylinder lens assemblies, means for positioning a particular lens in front of the sight axis, axis control means for controlling the axis of each cylinder lens, a cross-cylinder assembly which is synchronously coupled with said cylinder lens assemblies. The improvement of such type of refractor comprises the positioning means including an internally threaded cylinder axis drive gear having a lock shaft, said gear located outside of the housing and having its lock shaft extending through an opening in the housing coincident with the common axis of both carriers, said shafted cylinder axis drive gear riding upon bearing means disposed between it and the housing. The housing opening for the lock shaft has a sleeve within the housing which circumscribes the opening. There is an annular space formed between the lock shaft and the sleeve. The sleeve retains a first bearing means followed by a first said carrier, the shaft of a shafted cell drive gear then fitting between the annular space formed between the sleeve and the lock shaft and locking onto said lock shaft for synchronous movement of said cell drive gear and said axis drive gear. Bearing means then are fitted between the cell drive gear and the first carrier. A second carrier then fits over said lock shaft with bearing means disposed between the second carrier and the cell drive gear. A threaded pin then screws into the internal threads in the lock shaft to secure both cylinder lens assemblies to the housing.

5 Claims, 3 Drawing Figures

REFRACTOR HAVING SIMPLIFIED CYLINDER LENS ASSEMBLY

BACKGROUND OF THE INVENTION

The present invention relates to ophthalmic instruments referred to as refractors and more particularly to a refractor having a simplified cylinder lens assembly for more efficient and economic servicing thereof.

Commonly, an ophthalmic instrument referred to as a refractor is employed for efficiently carrying out optical analysis. Typical refractors include a right and a left battery, each having an eye position for the patient before which any of a broad variety of disk mounted testing lenses may be positioned. These lenses may be spherical, exhibiting a broad range of powers, or cylindrical, again exhibiting power variations but with respect to alignment along plus and minus axes. The cylindrical lenses may be used in the well-known Jackson cross-cylinder technique wherein the utilization of two cylinders off axis further is contrasted against a third spherocylindrical combination. The Jackson cross-cylinder test has been recognized as most beneficial to analysis and has been implemented broadly in ophthalmic refractors. An excellent explanation of the Jackson cross-cylinder test can be found in commonly assigned application Ser. No. 513,707 filed on July 14, 1983, of Marlin O. Thurston, now U.S. Pat. No. 4,523,822, the disclosure of which expressly is incorporated herein by reference.

Implementation of the Jackson cross-cylinder test in ophthalmic refractors has sparked various techniques for improving the accuracy of such test while reducing the burden and chance of error of the clinician administering such test. One such technique is the synchronization of the cross-cylinder lens in a manner wherein the axes of the cylinder lens and cross-cylinder lens are aligned in parallel at all times throughout administration of such ophthalmic evaluation. Initial efforts at developing such synchronization can be shown in U.S. Pat. Nos. 3,498,699 and 3,860,330, for example. Such techniques employ mechanical gear trains which link control knob means to the cylinder lens assemblies and to the cross-cylinder lens assembly whereby their axes remain parallel at all times. A much improved technique for such cross-cylinder synchronization involve optical encoding as described by Marlin O. Thurston in commonly-assigned application Ser. No. 513,707, cited above. Regardless of whether a mechanical or an electronic approach to the cross-cylinder synchronization is employed, all ophthalmic refractors must be serviced periodically for maintaining their efficiency and useful life. Moreover, mechanical defects often must be remedied in the refractor.

Servicing of ophthalmic refractors necessarily involves the skill of a trained technician who must be able to diagnose the instruments malady as well as repair same. For routine and warranty servicing, as well as for correction of defects in the instrument, repair time often dictates the ultimate cost involved in the reparation task. In this connection, disassembly of the refractor often is a simple task with the main burden of servicing falling upon reassembly. Reassembly of the instrument necessarily involves the realignment and timing of all mechanisms within the refractor so that accuracy and synchronization is maintained. For refractors which have the noted cross-cylinder synchronization feature, alignment of the timing of the instrument is even more critical.

The present invention provides a simplified assembly technique of the cylinder lens assemblies which is mechanically more reliable as well as simpler to service.

BROAD STATEMENT OF THE INVENTION

The present invention is directed to a refractor of the type having a housing which has a patient eye position for viewing along a sight axis extensible therethrough. The housing retains a pair of superimposed cylinder lens assemblies, each assembly having carriers rotably mounted for rotation about a common axis. Each carrier retains a plurality of rotable lens cells which contain at least one lens each. The refractor further is of the type having means for positioning select said lens cells into an aligned orientation with the sight axis and axis control means engageable with a positioned said cylinder lens cell for effecting the rotation to a select cylinder axis orientation. The refractor additionally is of a type having a cross-cylinder assembly operative in axis and power modes mounted upon the housing and having cross-cylinder lens means with a select power axis, rotatable lens mount means supporting said cross-cylinder lens means and movable to position said cross-cylinder lens in alignment with said sight axis; and means coupling said cylinder lens assemblies and said cross-cylinder assembly to synchronously maintain axes in parallel at all times. The improved refractor comprises the positioning means including an internally threaded cylinder axis drive gear having a lock shaft, said gear located outside of said housing and having its lock shaft extending through an opening in said housing coincident with the carriers' common axis, said shafted cylinder axis drive gear riding upon bearing means disposed between it and said housing. Said housing opening for the lock shaft has a sleeve within the housing which circumscribes the opening therethrough. There is an annular space created between the lock shaft and said sleeve. The sleeve retains first bearing means followed by a first said carrier, the shaft of a shafted cell drive gear fitting between the annular space formed between the sleeve and the lock shaft. The shaft of the shafted cell drive gear locks onto said lock shaft for maintaining simultaneous and synchronous movement of the cell drive gear and the axis drive gear. Also, there are bearing means between the cell drive gear and the first carrier. A second carrier then fits over the lock shaft, there being means disposed between the second carrier and the cell drive gear. Preferably, the bearing means is retained within a recess in the cell drive gear on one side and within a recess in the second carrier on the other side. A threaded pin screws into the internal threads in the lock shaft to secure both of the cylinder lens assemblies to the housing.

Advantages of the present invention include a cylinder lens assemblage which is simplified in construction, yet is mechanically reliable and efficient. Another advantage is a cylinder lens assembly which is accessible from the inside of the instrument without the need to disassemble any cylinder control knob or cross-cylinder assembly on the outside front of the refractor. A further advantage of a cylinder lens assemblage which is specifically designed for easy alignment of its timing during assembly. These and other advantages of the present invention will be readily apparent to those skilled in this art field based upon the disclosure contained in this application.

The drawings will be described in detail in connection with the Detailed Description of the invention which follows.

DETAILED DESCRIPTION

The refractor shown in U.S. Pat. No. 3,498,699 provides a mechanical geared synchronized drive to the cross-cylinder and can be modified according to the precepts of the present invention to provide a simplified cylinder lens assembly construction. The preferred refractor for modification, however, is the Thurston refractor disclosed in commonly assigned application Ser. No. 513,707. The majority of description, accordingly, will specifically refer to the Thurston refractor, though it must be understood that other refractors may be modified in accordance with the precepts of the present invention.

Figure 1:
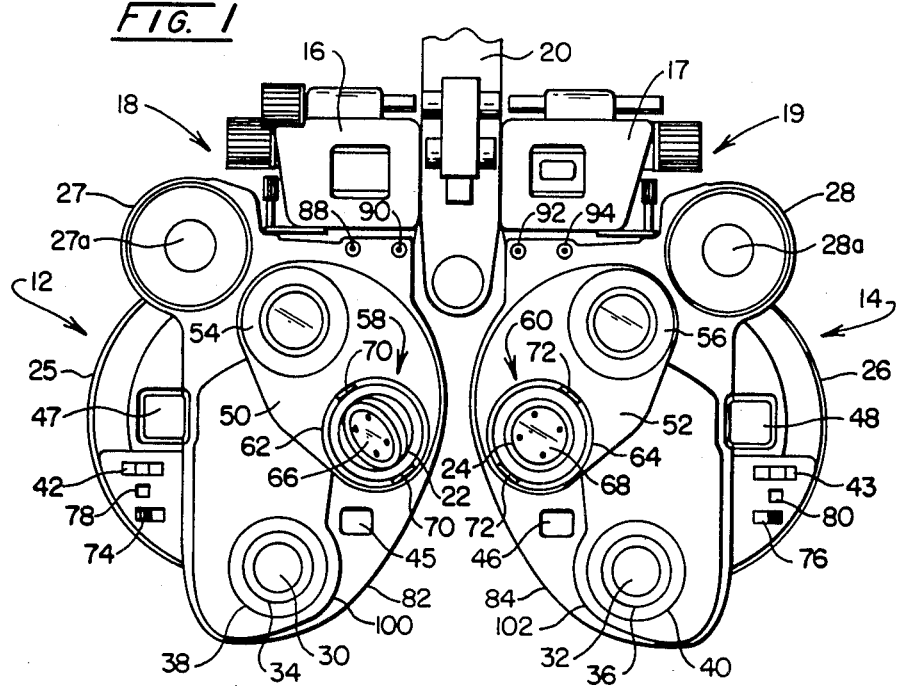
FIG. 1 is a front view of a refractor structured in accordance with the invention.

The housing for a refractor structured in accordance with the instant invention bears a close similarity to refractors which have been utilized by practitioners over a considerable period of time. Thus, which incorporating features permitting higher accuracy and reliability, the device as so structured enjoys an advantageous familiarity for the practitioner with respect to its use and inculcates a continued confidence in its utility for providing optimum services to the patient. Referring to FIG. 1, a refractor is depicted generally at 10 as is observed typically from a practitioner's position and is seen to include two substantially identical batteries, a right eye battery being represented at 12 and a left eye battery being represented at 14. These batteries 12 and 14 are supported by a bridging structure having components represented generally at 16 and 17 which, in turn, are connected with a yoke type assembly 20 which extends to a refractor arm (not shown), in turn, supported by an ophthalmic instrument stand (not shown). Various eye span and leveling adjustments are provided within the support components 16 and 17 to accommodate for individual patients. For example, leveling and interpupillary adjustment knobs are provided for each of the batteries 12 and 14 are represented, respectively and in general at 18 and 19. As is described in detail, for example, in U.S. Pat. No. 3,498,699, each battery of the refractor 10 carries a collection of lenses which are supported within rotatable disks which the practitioner may position in alignment with viewing tubes at which the patient's eye is positioned. These viewing tubes represent the sight axis for the testing system and are located at 22 in battery 12 and at 24 in battery 14.

Each of the batteries contains a plurality of spherical lenses which conventionally are mounted about the periphery of an annular disk which may be rotated so as to position selected lenses before viewing tubes 22 and 24. In this regard, knurled outer portion 25 of one such disk is provided for maneuvering spherical lenses in battery 12, while a similar peripheral edge is provided at 26 in battery 14. Additionally, a strong sphere lens control knob is provided for batteries 12 and 14, respectively at 27 and 28. Positioned coaxially upon each of these control knobs 27 and 28, there may be provided an auxiliary lens control knob as shown at 27a and 28a.

Each of the batteries also contains a cylinder lens assembly formed of two disks, one such disk carrying a stronger collection of cylinder lenses about its periphery, and the other carrying a collection of weaker cylinder lenses such that they may be combined in a progressive power sequence through interconnection with a Geneva intermittent drive. The latter drive is manipulated by a control knob as shown at 30 on battery 12 and at 32 on battery 14. While control knobs 30 and 32 serve to position successive cylinder lenses before respective viewing tubes 22 and 24, the cylinder axis for each such positioned cylinder lens may be controlled by rotative manipulation of an axis control knob 34 at battery 12 and 36 at battery 14. Power readouts identifying the cylinder lenses of the associated disk assembly are set forth in numeric fashion at windows 45 and 46, while spherical readouts are provided at windows 47 and 48 of respective batteries 12 and 14. Thus, as the patient observes an illuminated distant target through either of the viewing tubes 22 or 24, the practitioner may manipulate the associated axis control knob 34 or 36 to adjust the orientation of the cylinder axis of the cylinder lens then before the viewing tube. Additionally, cylinder power control knobs 30 and 32 may be manipulated. A protractor-type scale as at 38 on battery 12 and 40 on battery 14 is provided which carries indicia in degrees from 0 to 180 which may be read in conjunction with a pointer on respective control knobs 34 and 36 to show the axis orientation of the cylinder lens at the viewing tubes. For the instant purppose, this scale is provided merely for the convenience of the operator, its presence being somewhat redundant. Accordingly, the scales are graduated in broad, 15° increments of axis orientation. However, in the past, such scales were graduated in five degree increments to show the position of cylinder leans axis at the viewing tube. Control of the axis orientation of these cylinder lenses is by a sun-planet type gear association in typical refractor designs.

The cylinder lens axis orientation otherwise determined by the practitioner from scales 38 and 40 is replaced with the instant refractor by a solid-state illuminated three digit readout at displays 42 and 43 in respective batteries 12 and 14. The digits of these readouts may be provided as multi-segment LEDs which when energized are readily received by the practitioner even through operating in the low ambient lighting environment required to carry out clinical refraction. In the past, errors have been observed in interpolating the earlier five degree increments of axis orientation provided by scales read in conjunction with the axis control knobs. The instant refractor 10 will be seen to provide accurate readouts readily within one degree increments without interpolation.

The Jackson cross-cylinder test conventionally is practiced using a cross-cylinder lens mounted upon a rotative lens mount which, in turn, is supported upon a pivotal by-loupe turret. One such turret is pivotally mounted on each battery of the refractor in a manner such that the practitioner rotates the turret to an orientation wherein the cross-cylinder lens is aligned with an associated battery viewing tube. FIG. 1 shows turret 50 pivotally mounted upon battery 12 and corresponding turret 52 mounted upon battery 14. Turrets 50 and 52 each support a rotary prism lens system shown respectively at 54 and 56, as well as a cross-cylinder assembly as shown, respectively, at 58 and 60. In conventional fashion, each of the assemblies 58 and 60 includes a rotatable lens mount shown, respectively, at 62 and 64 which supports a cross-cylinder lens as shown, respectively, at 66 and 68. Cross-cylinder lenses 66 and 68 may be pivotally rotated about a flip axis by the manual movement of a pivoting assembly extending to oppositely disposed knurled knobs as shown at 70 in conjunction with lens 66 and at 72 in conjunction with lens 68. FIG. 1 shows that cross-cylinder lens 66 is in an orientation wherein it is being rotated or pivoted about its flip axis. In the past, the axial orientation of the cross-cylinder lens as at 66 was synchronized with the cylinder axis positioned before an associated viewing tube as at 22 by virtue of a geared connection of both with axis control knob 34, it being understood that a similar arrangement was provided in conjunction with control knob 36 and cross-cylinder lens 68.

The particular axis or power mode utilized for the cross-cylinder testing procedures is selected by the practitioner utilizing a slide switch mounted upon each battery 12 and 14 as shown, respectively at 74 and 76. The orientation of these switches is positively represented by illuminated mode displays shown, respectively, at 78 and 80. For example, the display provided at 76 and 80 may be a typical seven-segment light emitting diode which is energized to shown an "A" for axis mode operation and, correspondingly, a "P" for power mode operation.

Figure 2:
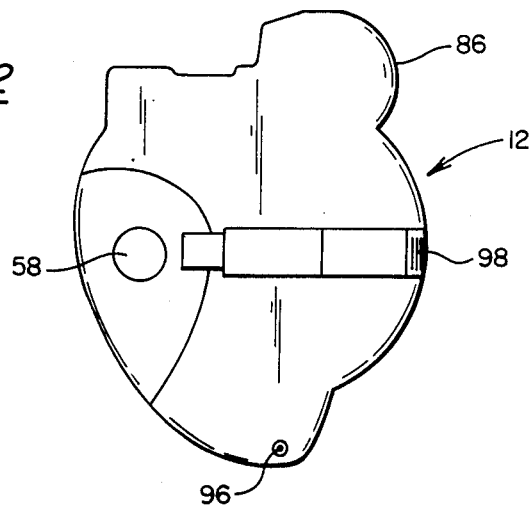
FIG. 2 is a rear view of the refractor of FIG. 1.

In order to gain access into batteries 12 and 14, removal of knobs 27 and 27a, and 28 and 28a, respectively, need be undertaken. The internal components within batteries 12 and 14 are retained within housings which comprise front portion 82 for battery 12 and front portion 84 for battery 14. The front housing portions are connected to back housing portions, such as back housing portion 86 for battery 12 depicted in FIG. 2. The corresponding back housing for battery 14 is not shown as it is identical in construction to back portion 86, but a mirror image thereof. Gaining access inside the housing, specifically referring to battery 12 for purposes of illustration, next requires the removal of screws 88 and 90 for battery 12 and screws 92 and 94 for battery 14. The final screw is removed from the lower portion of the housing as shown for back portion 86 for battery 12 in FIG. 2 as screw 96. A corresponding lower screw similarly is provided for battery 14. Referring to FIG. 2 in more detail, the conventional corneal alignment system 98 (eg. vertex distance 13.75 mm) is contained on back housing portion 86 in conventional fashion. A similar corneal alignment system is retained on the back housing for battery 14, but is not shown as it is identical in construction to that system shown for battery 12.

It is important to note at this junction that prior refractors have utilized different mechanisms for retaining the cylinder lens assemblies within the batteries. For example, the assembly shown in U.S. Pat. No. 2,968,213 provides for access to the cylinder lens assemblies from within the battery housing; however, such refractor has no cross-cylinder synchronization feature. The refractor shown in U.S. Pat. No. 3,498,699, while providing for cross-cylinder synchronization, is constructed such that removal of the cylinder lens assemblies can be accomplished only by initial removal of knobs 27 and 27a on battery 12, removal of knobs 30 and 34, removal of scale 38 under knobs 30 and 34, and removal of the combined assembly of cover plate 100 and turret 50. A similar sequence for battery 14 requires removal of knobs 28 and 28a, knobs 32 and 32, removal of scale 40 under knobs 32 and 36, and the combined assembly of cover plate 102 and turret 52. Next, the front and back housing portions must be disassembled. Finally, an unlocking mechanism on the outside of each front housing portion 82 and 84 must be removed as well as a screw provided inside each housing. If the refractor requires servicing internally for the cylinder assemblies only, for example, such design is extremely inefficient and costly, especially for reassembly and realignment, because the entire mechanisms on the front of the refractor batteries must be removed. The present invention retains the avantages of cross-cylinder synchronization while providing a cylinder lens assemblage which is entirely accessed from within the housing requiring, referring to battery 12 for example, removal of knobs 27 and 27a, screws 88 and 90, and screw 96 for gaining access to within the housing. None of the outer components on the front face of the batteries need be disturbed.

Figure 3:
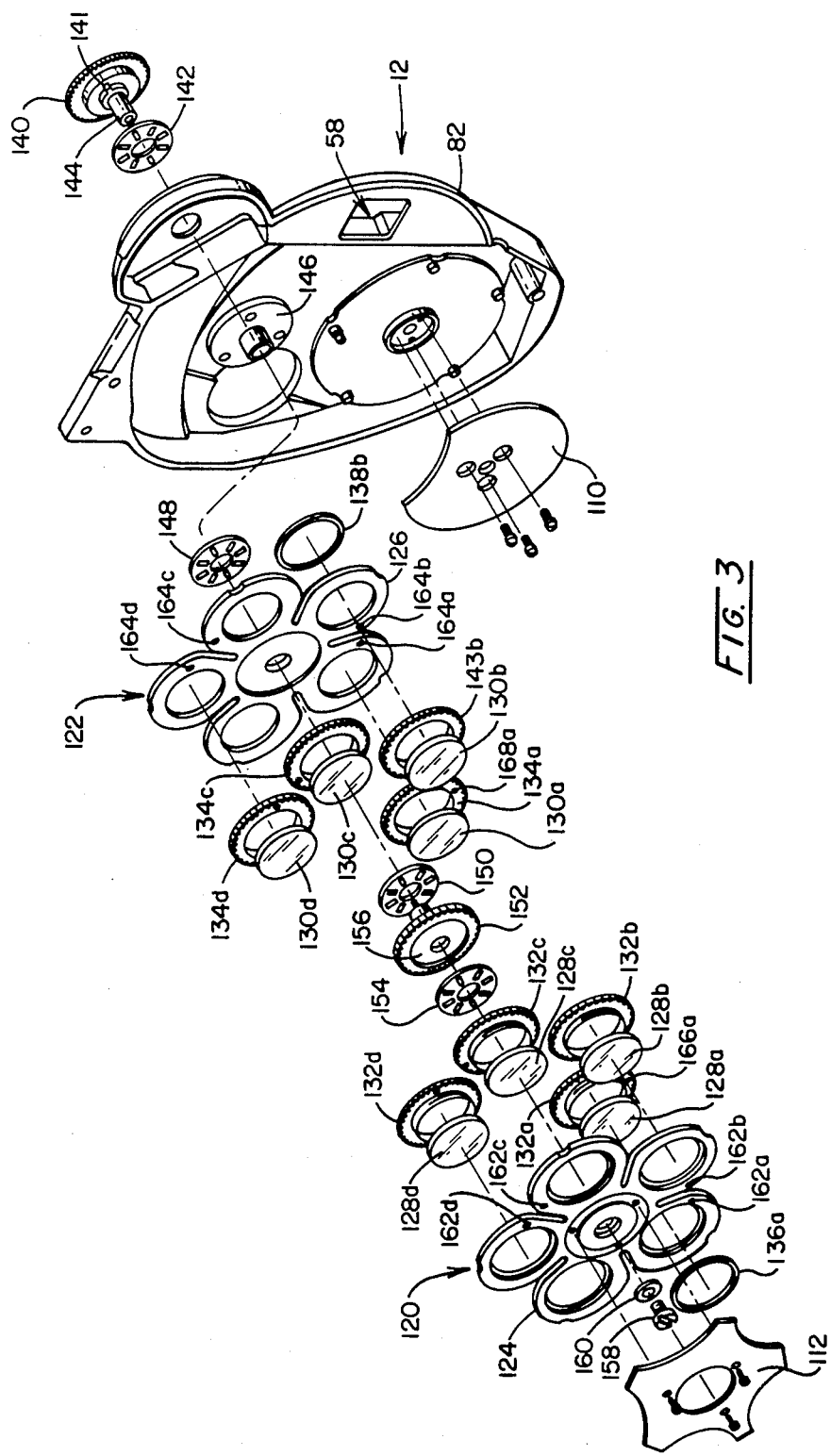
FIG. 3 is an exploded view of the cylinder lens assemblies of the present invention.

Referring to the novel cylinder lens assembly of the present invention. FIG. 3 provides the construction details of such assembly. FIG. 3 depicts battery 12 only and it must be understood that the internal construction of battery 14 is identical. The Geneva intermittent drive used to rotate the cylinder lens assemblies is conventional and shown in U.S. Pat. No. 2,968,213. Portions of such drive include locking plate (or more commonly moon) 110 and cylinder lock plate (or more commonly starwheel) 112. The operation of such Geneva intermittent drive from the outer control knobs through such assembly of parts will not be detailed here as specific reference to the cited patent is deemed sufficient. A strong cylinder lens assembly generally is represented at 120 and the weak cylinder lens assembly generally is shown at 122. Each assembly is composed of a carrier 124 and 126, respectively. Each carrier in turn retains lenses 128a–128d and 130a–130d, respectively. Note that each carrier 124 and 126 has an empty or vacant space which when rotated in front of viewing tube 58 permits lenses of the other assembly to be rotated in position for providing the only lens through which a patient looks. Moreover, combinations of lenses from both the strong and weak assemblies 120 and 122, respectively, can be utilized in conventional fashion. Each lens is retained within each carrier by circumferentially toothed cells 132a–132d for strong cylinder lens assembly 120 and circumferentially toothed cells 134a–134d for weak cylinder lens assembly 122. External retaining rings, which may be made of teflon or other plastically deformable or elastic material, 136a for cell 132a and 138b for cell 134b (only shown for illustration), complete the retention of the lens and cell assemblies within each respective carrier. The purpose of the circumferentially toothed cells will be described later.

Cylinder axis drive gear 140 is located on the front or outside of front housing portion 82 and provides the link or access of drive from the corresponding control knob located on the front of each battery to cylinder lens assemblies 120 and 122. Bearing means 142 is interposed between housing portion 82 and cylinder axis drive gear 140 for smooth and unbinded movement of such gear. Gear 140 bears integrally formed lock shaft 144 which fits through an opening in housing portion 82 to the interior of battery 12. The opening has sleeve 146 within the housing which circumscribes said opening. Carrier 126 fits over sleeve 146 and has bearing means 148 interposed about sleeve 146 between it and the interior of outside housing portion 82. Similar bearing means 150 is disposed on the reverse side of carrier 126. Next, shafted cell drive gear 152 has its shaft fitted within the opening in carrier 126. The shaft of cell drive gear 152 fits within an annular space created between sleeve 146 and lock shaft 144. The shaft on cell drive gear 152 has a slot or keyway which fits into key 141 on axis gear 140. The key and keyway locking mechanism is the means for transferring movement or rotation from cylinder axis drive gear 140 to cell drive gear 152. Cell gear 152 is circumferentially toothed and such teeth intermesh with the circumferential teeth about cells 132a–132d and 134a–134d for cylinder lens assemblies 120 and 122, respectively. The axis of each lens can have its axis adjusted via such arrangement.

Note should be taken that a minimum of rocking motion of carrier 126 is permitted by virtue of the unique arrangement of the shaft of cell drive gear 152, sleeve 146, and lock shaft 144. Next, bearing means 154 is placed on top of cell drive gear 152, preferably within race 156 on the outside of the cell drive gear 152. A similar race (not shown) preferably is formed on the back side of carrier 124 for receipt of bearing means 154. Carrier 124 next fits about lock shaft 144 which is of sufficient length to extend up through the opening in carrier 124. The entire assemblage described above then is secured by threaded pin 158 which desirably has washer 160 which washer distributes the forces exerted by pin 158 more evenly. Threaded pin 158 screws into internally threaded lock shaft 144 and is the sole means by which the entire cylinder lens assemblies are connected to front housing portion 82 of battery 12. Note that a double screw locking system may be substituted for pin 158 wherein an initial screw can be screwed into internally threaded lock shaft 144 for adjusting the tightness of the entire assemblage followed by an external screw for locking down the internal or first screw. Such alternative locking mechanisms, as well as others, are conventional in the art and need not be further expounded upon here. Suffice it to say that the arrangement of the cylinder lens assemblies depicted in FIG. 3 is entirely accessed from within each battery and does not require removal of turrets and other control knobs as prior refractors have required. Thus, when routine maintenance or problems (eg. warranty repairs) develop within the cylinder lens assemblies, quick access for repair can be gained without disturbance of the control knobs and other features external to each battery.

In this regard, note should be made of the holes shown on the annular portion of each carrier which annular portion retains the lenses and cells as described above. For carrier 124, these holes are shown as 162a–162d and for carrier 126 they are shown as holes 164a–164d. Each corresponding cell 132a–132d for carrier 124 and cell 134a–134d for carrier 126 similarly have holes within each circumferentially toothed annular cell which holes generally are shown at 166a for cell 132a and at 168a for cell 134a. The remaining cell holes are not individually labeled for easing over crowding of labeling on the drawing. Nevertheless, when the cylinder lens assemblies 120 and 122 are reassembled, the axis of each lens can be aligned automatically and simply by aligning the corresponding holes of each cell to each cell carrier of each cylinder lens assembly. Conveniently, a thin stiff pin can be placed down inside each pair of holes for simple alignment. When alignment of each cell is achieved, cell drive gear 152 will be engaged and complete alignment of the cylinder lens assemblies will be easily and accurately completed. Such method of aligning the cylinder lenses is yet another step forward in the unique assembly of the present invention.

It will be appreciated that various of the components shown and described herein may be altered or varied in accordance with conventional wisdom in the field and certainly are included within the present invention provided that such variations do not materially vary from the spirit and precepts of the present invention as described herein.

I claim:

1. A refractor of the type having a housing which has a patient eye position for viewing along a sight axis extensible therethrough;

a pair of superimposed cylinder lens assemblies within said housing, each assembly having carriers rotably mounted for rotation about a common axis, each said carrier retaining a plurality of rotable lens cells containing at least one lens;

means for positioning select said lens cells into an aligned orientation with said sight axis;

axis control means engageable with a positioned said cylinder lens cell for effecting the rotation to a select cylinder axis orientation;

a cross-cylinder assembly operative in axis and power modes mounted upon said housing and having cross-cylinder lens means with a select power axis, rotable lens mount means supporting said cross-cylinder lens means and movable to position said cross-cylinder lens in alignment with said sight axis;

means coupling said cylinder lens assemblies and said cross-cylinder assembly to synchronously maintain their axes in parallel at all times;

the improvement comprising:

said positioning means including an internally threaded cylinder axis drive gear having a lock shaft, said gear located outside of said housing and having its lock shaft extending through an opening in said housing coincident with said carriers' common axis, said shafted cylinder axis drive gear riding upon bearing means disposed between it and said housing;

said housing opening for said lock shaft having a sleeve within said housing circumscribing said opening, there being an annular space between said lock shaft and said sleeve, said sleeve retaining first bearing means followed by a first said carrier, the shaft of a shafted cell drive gear fitting between the annular space formed between said sleeve and said lock and locking onto said lock shaft for synchronous movement of said cell drive gear and said axis drive gear, there being bearing means between said cell drive gear and said first carrier;

a second said carrier then fitting over said lock shaft, there being bearing means disposed between said second carrier and said cell drive gear;

a threaded pin which screws into said internal threads in said lock shaft to secure both said cylinder lens assemblies to said housing.

2. The refractor of claim 1 wherein said cell drive gear contains a recess within which said bearing means interposed between said cell drive gear and said second carrier is disposed.

3. The refractor of claim 2 wherein said second carrier also has a recess for retaining said bearing means interposed between it and said cell drive gear.

4. The refractor of claim 1 wherein the annular portion of each said carrier which retains a lens and lens cell has a hole penetrating therethrough for aligning with a similar corresponding hole penetrating through each said lens cell.

5. The refractor of claim 1 wherein each said carrier has means for retaining five lenses each, and four lenses are retained within each said carrier.

* * * * *